US011938161B2

United States Patent
Sun et al.

(10) Patent No.: US 11,938,161 B2
(45) Date of Patent: Mar. 26, 2024

(54) USE OF GINSENG ALCOHOL EXTRACT IN SLEEP-PROMOTING HEALTH CARE PRODUCTS OR FOODS

(71) Applicant: Liwei Sun, Jilin (CN)

(72) Inventors: Liwei Sun, Jilin (CN); Rui Jiang, Jilin (CN); Daqing Zhao, Jilin (CN); Xiaohao Xu, Jilin (CN); Xuenan Chen, Jilin (CN); Jianzeng Liu, Jilin (CN); Rui Ma, Jilin (CN)

(73) Assignee: Sun Liwei, Jilin (CN)

( * ) Notice: Subject to any disclaimer, the term of this patent is extended or adjusted under 35 U.S.C. 154(b) by 0 days.

(21) Appl. No.: 17/560,772

(22) Filed: Dec. 23, 2021

(65) Prior Publication Data

US 2022/0202889 A1    Jun. 30, 2022

(30) Foreign Application Priority Data

Dec. 24, 2020 (CN) .......................... 202011549918.3

(51) Int. Cl.
| | |
|---|---|
| *A61K 36/258* | (2006.01) |
| *A61K 36/074* | (2006.01) |
| *A61K 36/076* | (2006.01) |
| *A61K 36/14* | (2006.01) |
| *A61K 36/254* | (2006.01) |
| *A61K 36/287* | (2006.01) |
| *A61K 36/48* | (2006.01) |
| *A61K 36/484* | (2006.01) |
| *A61K 36/725* | (2006.01) |
| *A61K 36/744* | (2006.01) |
| *A61K 36/79* | (2006.01) |
| *A61K 36/896* | (2006.01) |
| *A61K 36/8967* | (2006.01) |
| *A61P 25/20* | (2006.01) |

(52) U.S. Cl.
CPC .......... *A61K 36/258* (2013.01); *A61K 36/074* (2013.01); *A61K 36/076* (2013.01); *A61K 36/14* (2013.01); *A61K 36/254* (2013.01); *A61K 36/287* (2013.01); *A61K 36/48* (2013.01); *A61K 36/484* (2013.01); *A61K 36/725* (2013.01); *A61K 36/744* (2013.01); *A61K 36/79* (2013.01); *A61K 36/896* (2013.01); *A61K 36/8967* (2013.01); *A61P 25/20* (2018.01); *A61K 2236/13* (2013.01); *A61K 2236/333* (2013.01); *A61K 2236/37* (2013.01); *A61K 2236/53* (2013.01)

(58) Field of Classification Search
CPC .................................................. A61K 36/258
See application file for complete search history.

(56) References Cited

U.S. PATENT DOCUMENTS

2005/0031711 A1\* 2/2005 Park ..................... A61K 36/258
424/728

FOREIGN PATENT DOCUMENTS

KR            2057440 B1 \* 12/2019 ........... A23L 33/105

OTHER PUBLICATIONS

KR-2057440-B1 translated doc (Year: 2019).\*
Kim et al. (Ethanol Extract of the Flower Chrysanthemum morifolium Augments Pentobarbital-Induced Sleep Behaviors: Involvement of CI—Channel Activation, Evid Based Complement Alternat Med. 2011; 2011: 109164). (Year: 2011).\*

\* cited by examiner

*Primary Examiner* — Terry A McKelvey
*Assistant Examiner* — Jacob A Boeckelman
(74) *Attorney, Agent, or Firm* — Woods Oviatt Gilman LLP; Katherine H. McGuire, Esq.

(57) ABSTRACT

The present disclosure belongs to the technical field of health care products or foods and provides the use of a ginseng alcohol extract in sleep-promoting health care products or foods. Through analysis utilizing DAM2 drosophila behavior monitoring system, it is found that the ginseng alcohol extract can increase total sleep duration of normal and sleep deprived drosophilae, and relieve sleep rhythm disorder caused by sleep deprivation. Through a climbing experiment, it is found that the ginseng alcohol extract can improve the climbing ability of normal and sleep deprived drosophilae. The ginseng alcohol extract, on the one hand, improves the quality of sleep to protect the steady state of sleep rhythm, and on the other hand, increases the motive ability after sleep. The ginseng alcohol extract of the present disclosure is intended to be used to sleep-promoting health care products or healthy foods and improve the quality of sleep.

3 Claims, 2 Drawing Sheets

USE OF GINSENG ALCOHOL EXTRACT IN SLEEP-PROMOTING HEALTH CARE PRODUCTS OR FOODS

CROSS REFERENCE TO RELATED APPLICATION

This patent application claims the benefit and priority of Chinese Patent Application No. 202011549918.3 filed on Dec. 24, 2020, the disclosure of which is incorporated by reference herein in its entirety as part of the present application.

TECHNICAL FIELD

The disclosure belongs to the technical field of health care products or foods, and particularly relates to the use of a ginseng alcohol extract in sleep-promoting health care products or foods.

BACKGROUND ART

Insomnia is usually manifested as symptoms such as difficulty falling asleep, early morning awakening, short deep sleep duration and dreaminess. Therefore, adverse reactions can be triggered, such as headache, fatigue, irritability, nausea, arrhythmia, hypertension, hypomnesis and decreased immunity. Persistent insomnia not only causes cardiovascular and cerebrovascular diseases, neurodegenerative diseases and aging, but also serves as a main incentive for the concurrent manifestations and further vicious circle in the process of the above diseases. At the present stage, the use of sleep-promoting health care products that depend on medicine components such as melatonin has certain side effects, such as dependence, rebound due to withdrawal, long half-life, daytime sleepiness and other adverse consequences. Thus, traditional Chinese medicine-based sleep-promoting health care products without side effects and dependence have certain advantages in such the products.

In traditional Chinese medicine, insomnia is also referred to as being sleeplessness, which is caused by loss of energy or by uneasiness. It is usually treated with a "tranquilizing" medicine. Ginseng has the effect of "tranquilizing the mind", which was first seen in "Shen Nong's Materia Medica": "Soothe the spirit, calm the soul, and stop the palpitations".

The ginseng alcohol extract is a mixture of active substances in ginseng, which has a hypoglycemic effect, and is conventionally used for researches on treatment mechanism of diabetes (Treatment Mechanism Research of Ginseng alcohol extract on Diabetes Mice Model, Junxia Wang, Beijing Traditional Chinese Medicine, February 2011, Volume 30, Issue 2: 146-149). The combined use of the ginseng alcohol extract with other traditional Chinese medicine extracts also has the effect of delaying endothelial cell aging (Influence of Ginseng, Notoginseng and Chuanxiong Alcohol Extract on Autophagy of Aging Human Cardiac Microvascular Endothelial Cells, Wang Qiang, Journal of Traditional Chinese Medicine, Issue 6, 2017, 516-519). However, there have been no reports about the function of the ginseng alcohol extract to regulate sleep so far.

SUMMARY

In view of this, the objective of the disclosure is to provide the new use of the ginseng alcohol extract, that is, the use of the ginseng alcohol extract in sleep-promoting health care products or foods.

The disclosure provides the use of a ginseng alcohol extract in sleep-promoting health care products or foods.

The present disclosure further discloses a method for preparing the ginseng alcohol extract, wherein the method comprises the following steps: soaking washed ginseng in an alcohol aqueous solution having a volume concentration of 75-95%, subjecting the washed ginseng to reflux extraction via heating and to solid-liquid separation, and drying the resulting liquid phase to obtain the ginseng alcohol extract.

In one embodiment of the present disclosure, the alcohol aqueous solution is an ethanol aqueous solution or a methanol aqueous solution.

In one embodiment of the present disclosure, a ratio of the mass of ginseng to the volume of alcohol aqueous solution is 1 g:(6-8) mL.

In one embodiment of the present disclosure, the method further comprises a step of extracting ginseng residues with an aqueous solution of alcohol, following extraction with water under reflux.

In one embodiment of the present disclosure, a mass ratio of ginseng to water is 1:(6-8).

The time for water extraction is 1-2 h.

In one embodiment of the present disclosure, the time for alcohol aqueous solution soaking is 2-3 h.

The present disclosure further provides a composition comprising the ginseng alcohol extract containing 30-60% by weight of ginseng oligosaccharide and 5-10% by weight of ginsenoside as active components.

In one embodiment of the composition of the present disclosure, the composition further comprises one or more of extracts selected from the group consisting of a ginseng alcohol extract, a *Ziziphus jujuba* spinosa kernel extract, a *Ganoderma lucidum* extract, a cypress kernel extract, a poria cocos extract, a schisandra chinensis extract, a lily extract, a lotus seed extract, a chrysanthemum extract, a licorice extract, a saffron extract, a gardenia extract and an acanthopanax senticosus extract.

Provided is the use of the ginseng alcohol extract provided by the disclosure in sleep-promoting health care products or foods. Experiments of the disclosure prove that the ginseng extract can effectively relieve sleep rhythm disorder and reduction in exercise function that are caused by sleep deprivation. This shows that this ginseng extract can effectively improve the quality of sleep and increase the time of sleep. Therefore, it is intended to be developed into a health care product or food raw material capable of promoting sleep and adjusting the quality of sleep.

DETAILED DESCRIPTION OF THE EMBODIMENTS

Figure 1:
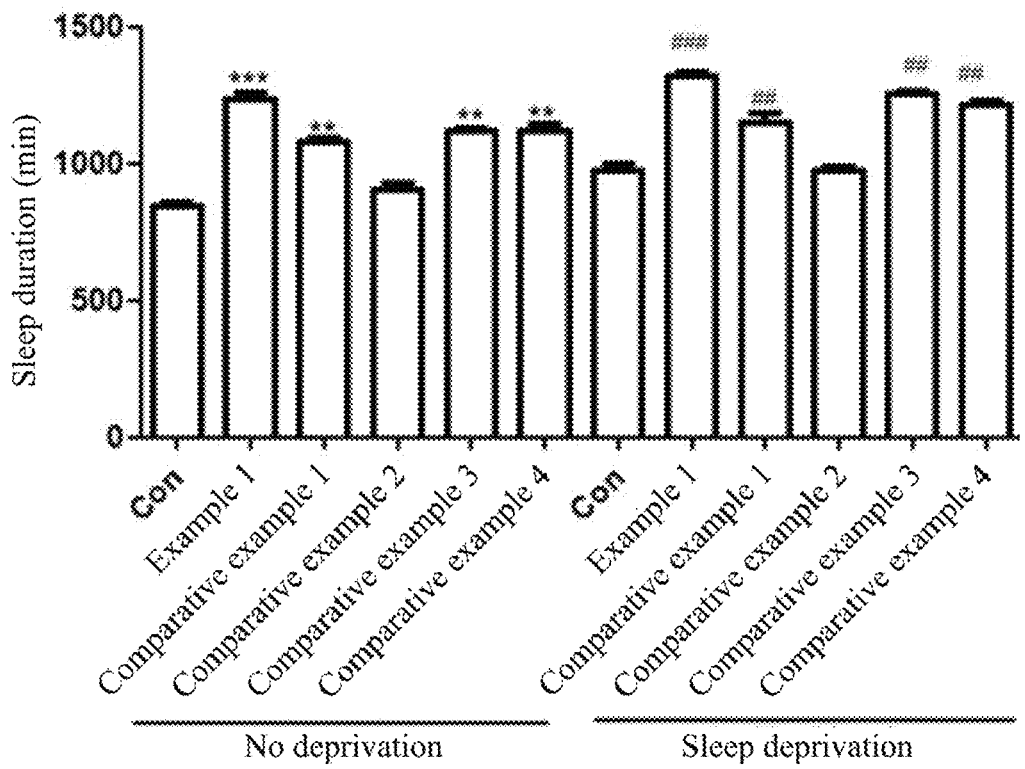
FIG. 1 shows influence of ginseng alcohol extract (as saponins of Panax japonicus, SPJ) and alcohol extracts prepared in various comparative examples on total sleep duration of normal and sleep deprived drosophilae, wherein, the normal sleep drosophilae in each group are compared with those in a blank group without medication (Con), the statistical results are expressed as (*) and wherein the sleep deprived drosophilae in each group are compared with those in the blank group without medication (Con), and the statistical results are expressed as (#).

The disclosure provides the use of a ginseng alcohol extract in sleep-promoting health care products or foods.

The disclosure further provides a method for preparing the ginseng alcohol extract, and the method comprises the following steps: soaking washed ginseng in an alcohol aqueous solution having a volume concentration of 75-95%, subjecting the washed ginseng to reflux extraction via heating and to solid-liquid separation, and drying the resulting liquid phase to obtain the ginseng alcohol extract. The alcohol aqueous solution is preferably an ethanol aqueous solution or a methanol aqueous solution, more preferably, an ethanol aqueous solution. A ratio of the mass of ginseng to the volume of alcohol aqueous solution is 1 g:(6-8) mL, more preferably, 1 g: 7 mL. The time of soaking the washed ginseng in the alcohol aqueous solution is preferably 10-14 h, more preferably, 12 h.

In the disclosure, before the washed ginseng is soaked in the alcohol aqueous solution, it is preferred that the washed ginseng is extracted with water, and the the solid phase obtained by reflux extraction via heating is extracted with the alcohol aqueous solution. The water extraction in advance is beneficial to removing excitatory substances in ginseng. A mass ratio of ginseng to water is 1:(6-8), more preferably, 1:7; the time for water extraction is 10-14 h, more preferably, 12 h; the time for alcohol aqueous solution extraction is 2-3 h. The temperature for alcohol aqueous solution extraction is 20-40° C., more preferably, 25° C. Low temperature extraction is beneficial to preventing precipitation due to cooling of liquid after alcohol-water extraction at a high temperature. The temperature for reflux extraction via heating is preferably 80-100° C., more preferably 90° C.; and the time for reflux extraction via heating is preferably 1.5-3 h, more preferably 2 h.

In the present disclosure, the obtained liquid phase is preferably subjected to concentration under reduced pressure prior to drying. Drying is carried out when the volume of the liquid phase is reduced to 5-10% of total volume. The drying is preferably carried out by spray drying. In the present disclosure, there is no special limitation to method of the spray drying, and drying methods known in the art can be adopted.

In the present disclosure, the ginseng alcohol extract comprises the following active components by weight: 30-60% of ginseng oligosaccharide, 5%-10% of ginsenoside and balanced active components such as tannin, flavones and polyphenol. By means of detection and verification, the remaining substances in the ginseng alcohol extract are not active components capable of improving sleep and do not dampen the overall effect.

In the present disclosure, the ginseng alcohol extract is preferably used in combination with one or more of extracts selected from the group consisting of a jujube kernel extract, a *Ganoderma lucidum* extract, a cypress kernel extract, a poria cocos extract, a schisandra chinensis extract, a lily extract, a lotus seed extract, a chrysanthemum extract, a licorice extract, a saffron extract, a gardenia extract and an acanthopanax senticosus extract in sleep-promoting health care products or foods. The jujube kernel extract, the *Ganoderma lucidum* extract, the cypress kernel extract, the poria cocos extract, the schisandra chinensis extract, the lily extract, the lotus seed extract, the chrysanthemum extract, the licorice extract, the saffron extract, the gardenia extract and the acanthopanax senticosus extract are water extracts and alcohol extracts commonly known in the art. In the above combined application scheme of the disclosure, the proportion of each extract is not specially limited, the ginseng alcohol extract can be compounded, in any ratios, with any one or more extracts selected from the jujube kernel extract, the *Ganoderma lucidum* extract, the cypress kernel extract, the poria cocos extract, the schisandra chinensis extract, the lily extract, the lotus seed extract, the chrysanthemum extract, the licorice extract, the saffron extract, the gardenia extract and the acanthopanax senticosus extract.

In the present disclosure, it is found by utilizing a drosophila behavior real time monitoring system that the ginseng alcohol extract can relieve sleep rhythm imbalance and reduction in motive function caused by sleep deprivation. Through comparison of proteome expression profiles of the drosophila brain tissue, sleep deprivation can significantly reduce the energy metabolism of brain tissues and expression of anti-oxidant related proteins, and the ginseng alcohol extract can reverse the change and restore to a normal expression level. Therefore, the ginseng alcohol extract can be applied to health care products or foods having the functions of promoting sleep and improving the quality of sleep. The addition amount of the ginseng alcohol extract is 10-25% of the total mass of health care products or foods. In the present disclosure, there is specific limitation to preparation methods of health care products or foods, and the preparation methods of health care products or foods known in the art may be adopted.

Next, the use of the ginseng alcohol extract in sleep-promoting health care products or foods provided by the present disclosure will be described in detail in combination with examples, but these examples cannot be understood as limiting the protection scope of the present disclosure.

Example 1

Preparation Method of Ginseng Alcohol Extract

The ginseng roots were washed and weighed, and then cut into 2 mm slices. 25 kg of ginseng slices were put into an extraction tank, and soaked for 10 h in 6 folds of softened water by weight at room temperature. The liquid in the tank was discharged after reflux extraction via heating for 2 h. Eight folds of softened water was added again for repeated extraction for 2 h, and ginseng residues were left in the tank for later use.

Six folds of 80% ethanol aqueous solution was added into the ginseng residues in the tank, the ginseng residues were leached for 12 h at a normal temperature of 25° C. under stirring. The liquid was discharged after extraction, filtered in a multi-stage pipeline filter and then pumped into a concentration tank. Reduced pressure concentration was performed in the concentration tank until 5% of volume was left, and the ginseng alcohol extract was obtained by spray drying.

Example 2

Preparation Method of Ginseng Alcohol Extract

Ginsengs were washed and weighed, and then and cut into 2 mm slices. 25 kg of ginseng slices were put into an extraction tank, and soaked in 7 folds of 95% ethanol by weight at a normal temperature of 25° C. for 3 h. Solid-liquid separation was carried out after soaking, filtrate was collected and put into a concentration tank and meanwhile 7 folds of 95% ethanol was added into the ginseng residues in the extraction tank, the ginseng residues were leached for 3 h at 25° C. under stirring. The liquid was discharged after extraction, filtered in a multi-stage pipeline filter and then pumped into a concentration tank. Reduced pressure concentration was performed in the concentration tank until 10% of volume was left, and the ginseng alcohol extract was obtained by spray drying.

Example 3

Preparation Method of Ginseng Alcohol Extract

Ginseng roots were washed and weighed, and then and cut into 2 mm slices. 25 kg of ginseng slices were put into an extraction tank, and soaked in 6 folds of methanol at 25° C. for 12 h. The liquid in the tank is discharged after leaching for 2 h at room temperature; 8 folds of methanol aqueous solution having a volume concentration of 80% was added again, and leaching was carried out for 2 h at room temperature, this processes were repeated twice, the liquid was discharged, filtered in a multi-stage pipeline filter and then pumped into the concentration tank Reduced pressure concentration was performed in the concentration tank until 5% of volume was left, and the ginseng alcohol extract was obtained by spray drying.

Comparative Example 1

Preparation Method of Ginseng Alcohol Extract

Ginseng roots were washed and weighed, and then and cut into 2 mm slices. 25 kg of ginseng slices were put into an extraction tank, and soaked with 6 folds of softened water by weight at room temperature for 12 h. The liquid in the tank was discharged after reflux extraction via heating for 2 h at 100° C. Six-fold softened water was added again, and extraction was repeated for 4 h, and the ginseng residues were left in the tank for later use.

Six folds of 60% ethanol was added into the ginseng residues in the tank, the ginseng residues were leached for 12 h at 25° C. under stirring. The liquid was discharged after extraction, filtered in a multi-stage pipeline filter and then pumped into a concentration tank Reduced pressure concentration was performed in the concentration tank until 10% of volume was left, and the ginseng alcohol extract was obtained by spray drying.

Comparative Example 2

Preparation Method of Ginseng Alcohol Extract

Ginseng roots were washed and weighed, and then and cut into 2 mm slices. 25 kg of ginseng slices were put into an extraction tank, and soaked with 6 folds of softened water by weight at room temperature for 12 h; the liquid in the tank was discharged after reflux extraction via heating for 4 h at 100° C. Eight folds of softened water was added again, and extraction was repeated for 4 h, and the ginseng residues were left in the tank for later use.

Six times of 75% ethanol was added into the ginseng residues in the tank, and the ginseng residues were leached for 12 h at 25° C. under the condition of stirring. The liquid was discharged after extraction, filtered in a multi-stage pipeline filter and then pumped into a concentration tank. Reduced pressure concentration was performed in the concentration tank until 10% of volume was left, and the ginseng alcohol extract was obtained by spray drying.

Comparative Example 3

Preparation Method of Ginseng Alcohol Extract

Ginseng roots were washed and weighed, and then and cut into 2 mm slices. 25 kg of ginseng slices were put into an extraction tank, and soaked in 8 folds of ethanol aqueous solution having a volume concentration of 50% at room temperature for 3 h under stirring. The liquid was discharged after extraction, filtered in a multi-stage pipeline filter and pumped into the concentration tank Reduced pressure concentration was performed in the concentration tank until 5% of volume was left, and the ginseng alcohol extract was obtained by spray drying.

Comparative Example 4

Preparation Method of Ginseng Alcohol Extract

Ginseng roots were washed and weighed, and then and cut into 2 mm slices. 25 kg of ginseng slices were put into an extraction tank, 8 folds of pure methanol by volume was added, and the liquid in the tank was discharged after reflux extraction via heating for 2 h at 100° C. Eight fold pure methanol was added again, and extraction was repeated for 2 h, and the ginseng residues were left in the tank for future use.

Example 4

The contents of sugar and saponin in ginseng alcohol extracts prepared in Examples 1-3 and Comparative examples 1-4 were measured by spectrophotometry, and their solubility and stability were compared.

The results show that the main active components in the ginseng alcohol extract are ginseng oligosaccharide and ginsenoside. The content of each component is calculated according to Formula I, Formula II and Formula III, and specific content results are shown in Table 1.

Yield (%) of ginseng alcohol extract=(ginseng alcohol extract/total ginseng mass)×100%    Formula I.

Ginseng oligosaccharide (%)=(ginseng oligosaccharide/ginseng alcohol extract)×100%    Formula II.

Ginsenoside (%)=(ginsenoside/ginseng alcohol extract)×100%    Formula III

TABLE 1

Components of ginseng alcohol extracts in Examples 1-3 and Comparative examples 1-4.

| Groups | Ginseng oligo-saccharide (%) | Ginsenoside (%) | Total amount (kg) of ginseng alcohol extract | Yield (%) of ginseng alcohol extract |
|---|---|---|---|---|
| Example 1 | 46.58 | 8.46 | 0.91 | 3.65 |
| Example 2 | 50.64 | 5.71 | 4.67 | 18.86 |
| Example 3 | 22.83 | 11.25 | 3.21 | 12.84 |
| Comparative example 1 | 53.45 | 3.59 | 1.54 | 6.16 |
| Comparative example 2 | 56.14 | 3.21 | 1.67 | 6.68 |
| Comparative example 3 | 53.85 | 2.68 | 5.4 | 21.67 |
| Comparative example 4 | 27.58 | 12.42 | 3.65 | 14.6 |

Note:
the extract in Comparative example 4 was precipitated out by standing after being formulated into a solution.

Example 5

Influence of Ginseng Alcohol Extract on Sleep Duration and Rhythm of Drosphilae 7-day-old male virgin drosophilae were divided into 4 groups, namely, blank group, blank medication group, sleep deprived group and sleep deprived plus medication group, with 32 drosophilae in each group. Administration was performed in an amount of 0.5% ginseng alcohol extract culture medium. Specifically, the ginseng alcohol extract was dissolved in the culture medium based on 0.5% by weight. 3 replicates were set. The 3 replicates were as follows: ginseng alcohol extracts (as SPJ) prepared in Example 1 were used respectively, and meanwhile a culture medium without the ginseng alcohol extract was used as a control, the prepared culture medium was foraged by drosophilae for 7 days in total, the blank group and the blank medication group were continued to be cultured under normal conditions for 12 h, the sleep deprived group and the sleep deprived medicine group were subjected to mechanical sleep deprivation in a shaker from 20:00 on that day to 8:00 am. on the next day. After sleep deprivation was ended, the drosophilae in each group were transferred to the DAM2 drosophila behavior analysis system, the action of drosophilae was monitored real time for 24 h, and the number 0 of activities within 5 minutes was used as the standard to judge that drosophila were in a sleep state.

Figure 2:
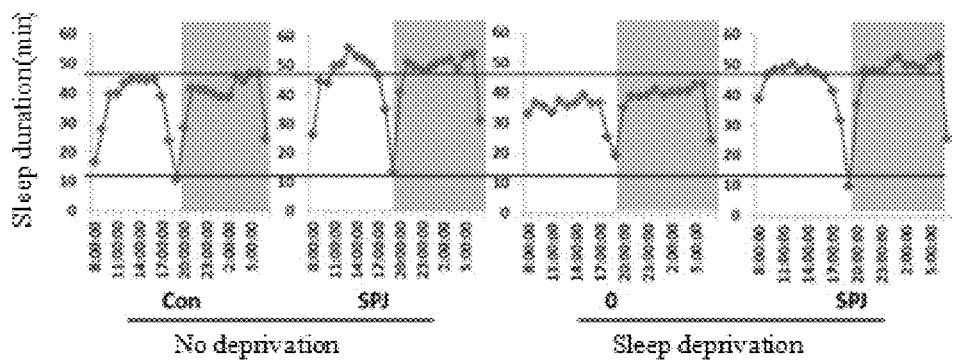
FIG. 2 shows influence of ginseng alcohol extract (SPJ) on sleep rhythm of normal and sleep deprived drosophilae.

The results are shown in FIG. 1 and FIG. 2. FIG. 1 shows the influence of ginseng alcohol extract (as SPJ) and alcohol extracts prepared in respective Comparative examples on total sleep duration of normal and sleep deprived drosophila. FIG. 2 shows the influence of ginseng alcohol extract (SPJ) on sleep rhythm of normal and sleep deprived drosophilae. The data prove that after the tested medicine of ginseng alcohol extract was added in Example 1, the total sleep durations of normal drosophila and sleep deprived drosophila increased by 46%±4.36% and 33.3%±2.80% ($p<0.001$) respectively. An increase in the total sleep duration of normal drosophila and sleep deprived drosophila could also be noted in Comparative examples 1, 3 and 4 by 23.87%±2.7% versus 18.99%±4.93% (Comparative example 1), 28.77%±1.91% versus 29.76%±1.84% (comparative example 3), and 28.85%±3.70% versus 25.61%±2.01% (comparative example 4), respectively, and the activities of drosophilae in three groups are lower than the activity of example 1 ($p<0.05$). The total sleep duration of two groups of drosophilae was not increased in Comparative example 2. This may be due to the over long heating which decreased the activity of sleep-promoting components in the extract and meanwhile long time extraction in aqueous solution increased the loss of alcohol-soluble oligosaccharide component having a sleep-promoting function. In addition, after the extracts obtained from refluxed ethanol and methanol extraction tended to form water insoluble floccules after restored to room temperature, which brought in many difficulties for post-treatment procedures.

The quality of sleep is not only related to the sleep duration but also related to sleep deepness. When evaluating sleep based on sleep amplitude, the larger the sleep amplitude is, the better the quality of sleep is. As shown in FIG. 2, after sleep deprivation, the sleep amplitude of drosophila is obviously shortened, which is similar to a state of being half asleep. After the ginseng alcohol extract (as SPJ) in Example 1 is added, the sleep amplitude is the same as that for normal drosophilae, which shows that ginseng alcohol extract has a potential effect on regulating the sleep rhythm.

Example 6

Influence of Ginseng Alcohol Extract on Climbing Ability of Drosophila

Bad sleep can affect the motive function of body, and influence of the ginseng alcohol extract in Example 1 on the motive function of sleep deprived drosophilae was evaluated.

7-day-old male virgin drosophilae were divided into 4 groups, namely, a blank group, a blank medication group, a sleep deprived group and a sleep deprived medication group, with 32 drosophilae in each group.

The above 4 groups of drosophilae were separately placed in a climbing plate, all the drosophilae were vertically knocked off, then photographs were taken in the $5^{th}$ second to record the climbing distances of drosophilae. Within the same time, the higher the climbing distance was, the stronger motive function was.

Figure 3:
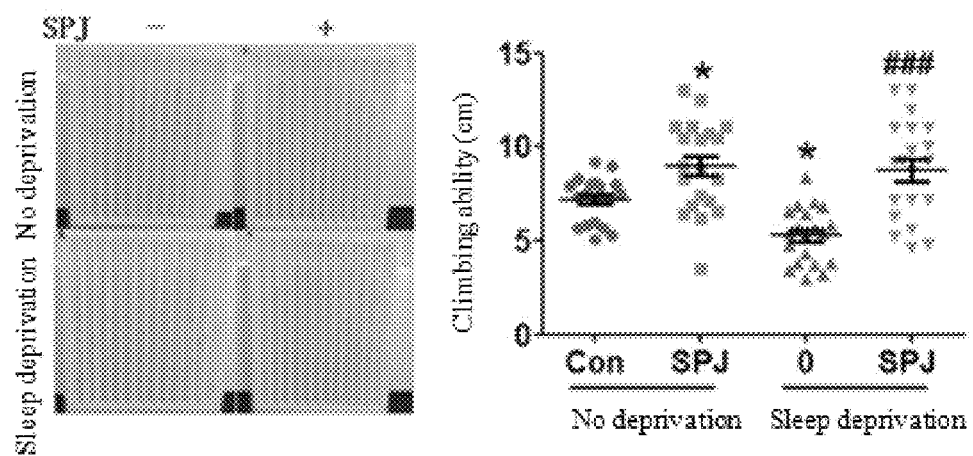
FIG. 3 shows influence of ginseng alcohol extract (SPJ) on climbing abilities of normal and sleep deprived drosophilae, wherein the normal sleep drosophila in each group are compared with those in a blank group without medication (Con), the statistical results are expressed as (*), wherein the sleep deprived drosophilae in each group are compared with those in the blank group without medication (Con), and the statistical results are expressed as (#).

The results are shown in FIG. 3. FIG. 3 shows the influence of ginseng alcohol extract (as SPJ) on climbing ability of normal and sleep deprived drosophilae. The results prove that sleep deprivation can reduce the motive function of the drosophilae. After the ginseng alcohol extract (SPJ) in Example 1 was administrated, the motive function of drosophila can be restored to a normal level ($p<0.05$).

It can be seen from the above examples that the ginseng alcohol extract (as SPJ) can significantly improve the total sleep duration of normal and sleep deprived drosophilae, and relieve the sleep rhythm disorder caused by sleep deprivation. That is, the sleep amplitude is restored to a normal level. Meanwhile, the ginseng alcohol extract (as SPJ) can improve the climbing ability of sleep deprived drosophilae and restore the motive function.

Described above are merely preferred embodiments of the disclosure. It should be note that a person of ordinary skill in the art can also make several improvements and modifications without departing from the principle of the disclosure, these improvements and modifications should also be deemed as falling within the protection scope of the disclosure.

What is claimed is:

1. A method for improving sleeping quality, comprising administering a health care product or food containing a ginseng alcohol extract to an individual in need, wherein the health care product or food containing a ginseng alcohol extract is obtained by a method comprising the following steps:
   extracting ginseng root with water under reflux to remove excitatory substances in the ginseng root, wherein a mass ratio of the ginseng root to water is 1:(6-8) and a time for water extraction is 1-2 h;
   collecting a ginseng residue after extracting with water;
   soaking the ginseng residue in an alcohol aqueous solution having an alcohol volume concentration of 75-95%;
   subjecting the ginseng residue to reflux extraction via heating and solid-liquid separation to produce a resulting liquid phase; and
   drying the resulting liquid phase to obtain the ginseng alcohol extract.

2. The method according to claim 1, wherein the ginseng alcohol extract comprises 30-60% by weight of ginseng oligosaccharide and 5-10% by weight of ginsenoside as active components.

3. The method according to claim 2, wherein the ginseng alcohol extract health care product or food further comprises one or more of extracts selected from the group consisting of a jujube kernel extract, a *Ganoderma lucidum* extract, a cypress kernel extract, a poria cocos extract, a schisandra chinensis extract, a lily extract, a lotus seed extract, a chrysanthemum extract, a licorice extract, a saffron extract, a gardenia extract and an acanthopanax senticosus extract.

\* \* \* \* \*